United States Patent [19]

Zweig et al.

[11] 4,273,764

[45] Jun. 16, 1981

[54] STABILIZATION OF 2,2-DIMETHYL-4,5-BENZOSPIRO[2,4]HEPTA-4,6-DIENE-1-CARBOXYLIC ACID, α-CYANO-M-PHENOXYBENZYL ESTER

[75] Inventors: Arnold Zweig, Westport; Arthur K. Hoffmann, New Canaan, both of Conn.

[73] Assignee: American Cyanamid Company, Stamford, Conn.

[21] Appl. No.: 70,758

[22] Filed: Aug. 30, 1979

Related U.S. Application Data

[60] Division of Ser. No. 685,944, May 13, 1976, which is a continuation-in-part of Ser. No. 470,763, May 17, 1974, abandoned, which is a continuation-in-part of Ser. No. 403,366, Oct. 4, 1973, abandoned.

[51] Int. Cl.³ .................... A01N 25/22; C07C 69/74; A01N 37/00; C07C 121/50
[52] U.S. Cl. .................. 424/174; 260/465 D; 424/175; 424/304; 424/306; 560/8
[58] Field of Search ............... 424/175, 304, 302, 174, 424/306; 260/465 D; 560/8

[56] References Cited

U.S. PATENT DOCUMENTS

| | | | |
|---|---|---|---|
| 2,011,428 | 8/1935 | Voorhees | 424/190 |
| 2,421,223 | 5/1947 | Smith et al. | 424/193 |
| 3,063,893 | 11/1962 | Goldberg et al. | 424/188 |
| 3,215,717 | 11/1965 | Foster | 260/439 |
| 3,313,770 | 4/1967 | Foster | 260/45.75 |
| 3,379,680 | 4/1968 | O'Konski | 260/45.75 |
| 3,560,613 | 2/1971 | Miskus et al. | 424/174 |
| 3,632,825 | 1/1972 | Jordan | 424/295 |
| 4,060,632 | 11/1977 | Addor | 424/306 |
| 4,087,523 | 5/1978 | Lovell | 424/304 |
| 4,171,355 | 10/1979 | Stubbs et al. | 424/174 |

OTHER PUBLICATIONS

J. Agr. Food Chem., 20(2), 313–315, (1972), Miskus et al.

*Primary Examiner*—Douglas W. Robinson
*Attorney, Agent, or Firm*—H. G. Jackson

[57] ABSTRACT

Resmethrin and 4,5-benzospiro[2,4]hepta-4,6-diene-1-carboxylic acid, α-cyano-m-phenoxybenzyl ester are stabilized against degradation with stabilizing amounts of nickel complexes of 2,2'-thiobis(p-alkylphenols).

6 Claims, No Drawings

STABILIZATION OF 2,2-DIMETHYL-4,5-BENZOSPIRO[2,4]HEPTA-4,6-DIENE-1-CARBOXYLIC ACID, α-CYANO-M-PHENOXYBENZYL ESTER

CROSS-REFERENCE TO RELATED APPLICATION

This is a division, of application Ser. No. 685,944 filed May 13, 1976, which is a continuation-in-part application of Ser. No. 470,763 filed May 17, 1974 now abandoned which is a continuation-in-part application of U.S. Ser. No. 403,366, filed Oct. 4, 1973, now abandoned.

BACKGROUND OF THE INVENTION

1. Field of the Invention

The invention pertains to the art of stabilization of pyrethroid insecticides against the deteriorative effects of light and air.

2. Description of the Prior Art

Pyrethroid insecticidal compositions have been used for many years to control common household pests, such as the housefly and mosquito. The popularity of pyrethroid insecticidal compositions stems from their rapid knock-down of these insects and from their low toxicity to warm-blooded animals. However, these desirable properties are to some extent offset by a rapid loss of potency when compositions containing the pyrethroid are exposed to sunlight.

Many methods are disclosed in U.S. Cl. 424–174 and 164–24 for the stabilization of pyrethroids.

SUMMARY OF THE INVENTION

Nickel complexes of 2,2'-thiobis-(p-alkylphenols) of the formula

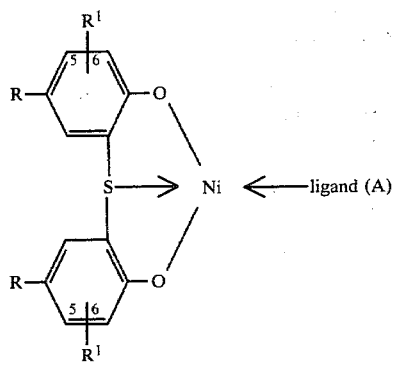

where R is an alkyl group of 6 to 10 carbon atoms, R' is hydrogen or an alkyl group of 6 to 10 carbon atoms and is positioned at the 5 or 6 position of the ring and the ligand (A) is water, ammonia or an aliphatic primary or secondary amine of 1 to 18 carbon atoms or an aromatic primary or secondary amine of 1 to 18 carbon atoms are stabilizers for resmethrin and 2,2-dimethyl-4,5-benzospiro[2,4]hepta-4,6-diene-1-carboxylic acid, α-cyano-m-phenoxybenzyl ester. The pyrethroid compositions of the invention are useful insecticides.

DESCRIPTION OF THE INVENTION INCLUDING PREFERRED EMBODIMENTS

The invention is compositions of matter comprising the pyrethroids resmethrin or 2,2-dimethyl-4,5-benzospiro-[2,4]hepta-4,6-diene-1-carboxylic acid, α-cyano-m-phenoxybenzyl ester and a stabilizing amount of a nickel complex of 2,2'-thiobis-(p-alkylphenol) as defined in the Summary, above. Preferred 2,2'-thiobis-(p-alkylphenols) are as defined in the Summary where R is an alkyl group of 6–10 carbon atoms, R' is a hydrogen or an alkyl group of 6–10 carbon atoms and is positioned at the 5 or 6 position of the ring and the ligand (A) is water, ammonia or an aliphatic primary or secondary amine of 1 to 18 carbon atoms. The invention includes a method of killing insects using the compositions of the invention. These stabilizers and methods for their manufacture are disclosed in U.S. Pat. Nos. 3,215,717; 3,218,294; 3,313,770; and 3,379,680.

Pyrethroids are normally degraded by sunlight within 2 to 4 hours. Stabilizing a pyrethroid with a nickel complex of 2,2'-thiobis-(p-alkylphenol) increases the effectiveness of the pyrethroid to 15.5 hours or more of sunlight exposure, thus greatly increasing the practical insecticidal effectiveness. The compound

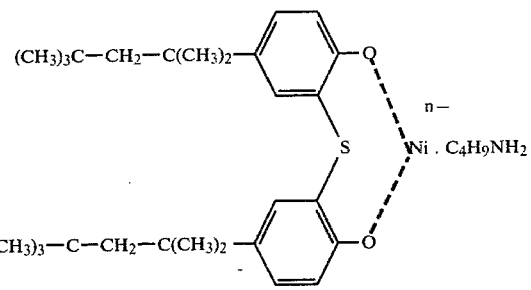

was formulated as an emulsifiable concentrate by mixing the stabilizer with an emulsifying agent and xylene as shown in Table I. This concentrate was then mixed with the pyrethroid (resmethrin) on a weight/weight basis in ratios of 10:1 and 1:1 (stabilizer:pyrethroid) based on a pyrethroid application rate of one half pound actual ingredient per acre.

TABLE I

|  | Weight in Grams |
|---|---|
| Stabilizer | 25.7 |
| Emulsifier | 6.4 |
| Xylene | 67.0 |
| Total | 100.00 |

A test solution was prepared by bringing the stabilizer/pyrethroid/solvent/emulsifier mixture up to spray volume with deionized water. The test solution was prepared in a brown glass bottle shortly before use.

The plants used for evaluation of the test solution were sieve lima bean plants in the top true leaf stage of growth and potted one plant in an 8 oz. paper cup. The test solutions were applied to the leaf surface of the plants with an overhead sprayer set on a moving track allowing it to be moved overtop the plants. The sprayer was fitted with Teejet ® nozzle No. SS65015 and calibrated to deliver known rates in the equivalent of 86 gallons of water per acre. After application, the bean plants were allowed to air dry approximately fifteen minutes at which time a zero hour bioassay sample was taken. The plants were placed outdoors on a table and exposed to the sun. Additional bioassay samples were taken at various intervals until 8 and one half hours of exposure as shown in Table II. The sky was cloudy to partly cloudy throughout the test period. The bioassay procedure used in the evaluation reported in Table II is as follows: Two treated bean leaves, one from each of two plants from each treatment, were excised and placed in individual 9.0 cm glass petri dishes which contained a moist filter paper and 10 third instar southern armyworm *Spotoptera eridania* larvae. These petri dishes were identified and kept in a holding room at 80° F., 50% relative humidity for 48 hours, at which time mortality counts were taken. These mortality data indicate that the stabilizer of the invention increased the residual activity of the pyrethroid to 8 and one half hours, the length of the test period. The stabilizer in Table II was formulated with the resmethrin at ratios of 1:1 and 10:1 (stabilizer:pyrethroid). The data is expressed as 48 hours percent mortality.

TABLE II

| Compound | Stabilizer/Pyrethroid Ratio | Hours of Exposure to Sunlight | | | | | | | |
|---|---|---|---|---|---|---|---|---|---|
| | | 0 | 2 | 3 | 4 | 5 | 6 | 7 | 8½ |
| Stabilizer and Resmethrin | 1:1 | 100 | 100 | 100 | 100 | 95 | 100 | 95 | 70 |
| Stabilizer and Resmethrin | 10:1 | 100 | 100 | 100 | 100 | 70 | 90 | 95 | 100 |
| Resmethrin | | 100 | 100 | 100 | 45 | 15 | 30 | 35 | 0 |
| CHECK | | 0 | 0 | 0 | 0 | 0 | 0 | 0 | 0 |

Using the same procedure as that described for Table II, the same compound was further evaluated to determine the total length of its activity. After application, the plants were set outdoors and bioassayed as in the previous test. After the 8 and one half hour sample, the plants were brought indoors and kept in a greenhouse overnight for 15 and one half hours (6:15 pm to 9:45 am) and then placed outdoors again and the bioassay schedule resumed. The sky was partly cloudy during the first five hours of the test and sunny throughout the remainder. The data obtained from this second evaluation and reported in Table III, below, shows that the stabilizer increased the foliar residual activity of the pyrethroid 3½ fold. The data in Table II is expressed and 48 hour percent mortality.

TABLE III

| Compound | Stabilizer/ Pyrethroid Ratio | Hours of Sunlight Total Hours of Test | | | | | | | | | | | | | | |
|---|---|---|---|---|---|---|---|---|---|---|---|---|---|---|---|---|
| | | 0 0 | 3 3 | 4 4 | 5 5 | 6 6 | 7 7 8½ | 8½ 24 | 8½ 25 | 9½ 26 | 10½ 27 | 11½ 28 | 12½ 29 | 13½ 30 | 14½ 31 | 15½ |
| Stabilizer and Resmethrin | 1:1 | 100 | 100 | 100 | 100 | 95 | 100 | 95 | 90 | 100 | 70 | 100 | 65 | 90 | 90 | 50 |
| Stabilizer and Resmethrin | 10:1 | 100 | 100 | 100 | 100 | 100 | 100 | 95 | 95 | 100 | 95 | 70 | 85 | 30 | 50 | 45 |
| Resmethrin | | 100 | 100 | 40 | 10 | 45 | 20 | 5 | 0 | 0 | 15 | 0 | 5 | 5 | 0 | 0 |
| Check | | 0 | 0 | 0 | 0 | 0 | 0 | 0 | 0 | 0 | 0 | 0 | 0 | 0 | 0 | 0 |

Resmethrin ($2.22 \times 10^{-3}$M) solutions in n-hexadecane containing approximately $5 \times 10^{-4}$M concentration of nickel complexes of 2,2'-thiobis-)p-alkylphenol) were irradiated with ~1300 ft. candles of light from a pyrex filtered 450 W Xenon sources for periods up to 24 hours to illustrate the stabilizing effect of the invention and the results are shown in Table IV, below. The source was chosen to closely match in sunlight spectrum. The samples were irradiated in quartz cells and analysis was performed by gas liquid chromatography (GLC). The half-life (t ½) values provide a good measure of relative stabilizer efficacy.

TABLE IV

| | Nickel Complex | | | Relative half-life |
|---|---|---|---|---|
| | R | R' | Ligand(A) | |
| Control | — | — | — | 1.0 |
| | t-octyl | H | n-butylamine | 1.5 |
| | t-octyl | H | n-$C_{12}H_{25}NH_2$ | 1.4 |

Preparation of 2,2-Dimethyl-4,5-benzospiro[2,4]hepta-4,6-diene-1-carboxylic acid, α-cyano-m-phenoxybenzyl ester.

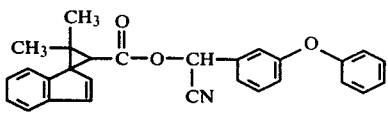

2,2-Dimethyl-4,5-benzospiro[2,4]hepta-4,6-diene-1-carboxylic acid, 3.4 g is dissolved in 100 ml of a hexane/benzene (4:1) solution. Thionyl chloride, 15.0 g is then added and the solution is stirred for 12 hours. Refluxing is carried out for 20 minutes, and the volume is reduced in vacuo to remove solvents and excess thionyl chloride. The acid chloride is used directly without further purification. The acid chloride is taken up in 20 ml of benzene and is added dropwise to a solution of 3.1 g of α-cyano-m-phenoxybenzyl alcohol and 1.0 g of pyridine in 100 ml of benzene. After 4 hours, the precipitate is filtered, and the filtrate reduced in vacuo to give a viscous oil. Purification by column chromatography on silica gel with elution by chloroform/hexane (1:2) gives 1.3 g of pale yellow oil which exhibits the following spectral properties: infrared spectrum (neat film) 1730 $cm^{-1}$; nuclear magnetic resonance spectrum ($CDCl_3$)$\delta$=6.8–7.6 (m, 14.5 H, aromatic and vinyl), 6.37

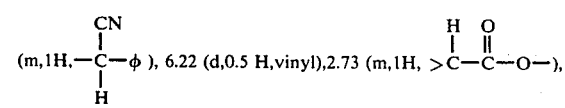

), 6.22 (d,0.5 H,vinyl),2.73 (m,1H, >C—C—O—), 1.72–1.43 (m, 6 H, methyls).

UV STABILIZATION OF 2,2-DIMETHYL-4,5-benzospiro[2,4]hepta-4,6-diene-1-carboxylic acid, α-cyano-m-phenoxybenzyl ester.

Purpose

To determine the effect of Compound I, above, on the residual insecticidal toxicity of the pyrethroid, 2,2-dimethyl-4,5-benzospiro[2,4]-hepta-4,6-diene-1-carboxylic acid, α-cyano-m-phenoxybenzyl ester.

Procedure 2,2-Dimethyl-4,5-benzospiro[2,4]hepta-4,6-diene-1-carboxylic acid, α-cyano-m-phenoxybenzyl ester (95% real) was formulated as a 10% active emulsifiable concentrate. The combination of 2,2-dimethyl-4,5-benzospiro[2,4]hepta-4,6-diene-1-carboxylic acid, α-cyano-m-phenoxybenzyl ester plus Compound I, above, was formulated as an emulsifiable concentrate containing 10% 2,2-dimethyl-4,5-benzospiro[2,4]hepta-4,6-diene-1-carboxylic acid, α-cyano-m-phenoxybenzyl ester and 30% Compound I.

Dilute emulsions of the two formulations were prepared with tap water to contain 300 ppm of 2,2-dimethyl-4,5-benzospiro[2,4]hepta-4,6-diene-1-carboxylic acid, α-cyano-m-phenoxybenzyl ester. Young cotton plants which had been grown for 30 days under high intensity lights were dipped in the dilute emulsion (each leaf for 3 seconds with agitation). The plants were allowed to dry when the zero day leaf samples were removed for assay with third-instar southern armyworms. The cotton plants were then removed to the greenhouse and placed under high intensity lights which emitted UV light. Additional leaves were excised for assay at 2, 3, 6, 10 and 13 days following treatment.

The assay procedure was to place a moistened Watman No. 1 filter paper in the bottom of a petri dish. The excised leaf was placed on the moistened paper with 10 third-instar southern armyworm larvae. Larval mortality counts were made after 72 hours and are reported as average percent mortality. Table V summarizes the results.

We claim:

1. A process for stabilizing 2,2-dimethyl-4,5-benzospiro[2,4]hepta-4,6-diene-1-carboxylic acid, α-cyano-m-phenoxybenzyl ester which comprises adding thereto in an amount to effect stabilization a compound of the formula:

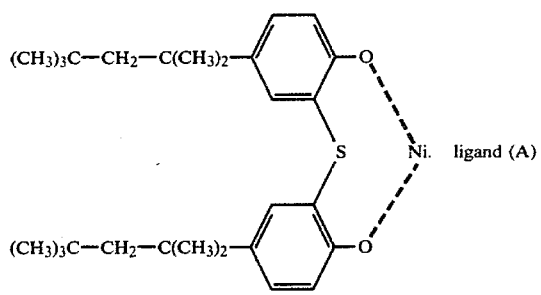

wherein the ligand (a) is an aliphatic primary amine of 4–12 carbon atoms.

2. A process according to claim 1 wherein the stabilizer is a compound of the formula:

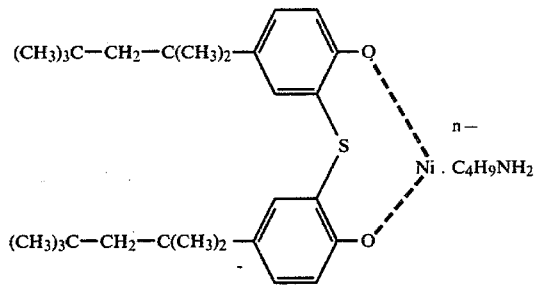

3. A process according to claim 1 wherein the stabilizer is a compound of the formula:

TABLE V 2,2-Dimethyl-4,5-benzospiro[2,4]hepta-4,6-diene-1-carboxylic acid, α-cyano-m-phenoxybenzyl ester + Compound I (1:3) Residual Insecticidal Activity Demonstrated with Southern Armyworms on Cotton Plants Under High Intensity Lights

| Compound | Rate ai (ppm) | Average Percent Mortality of Southern Army worms | | | | | |
|---|---|---|---|---|---|---|---|
| | | 0 Days | 2 Days | 3 Days | 6 Days | 10 Days | 13 Days |
| (pyrethroid structure) | 300 | 100 | 100 | 92.5 | 84.3 | 18.9 | 21.6 |
| (pyrethroid structure) + Stabilizer, Compound I | 300 | 97.5 | 95 | 98.8 | 96.3 | 88.9 | 87.5 |
| Check | — | 0 | 0 | 1.3 | 0 | 0 | 2.5 |

Results comparable to those reported in the Tables above are obtained with the other compounds useful as stabilizers in our invention.

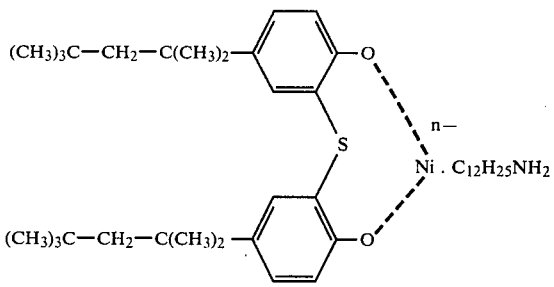

4. A stabilized 2,2-dimethyl-4,5-benzospiro[2,4]hepta-4,6-diene-1-carboxylic acid, α-cyano-m-phenoxybenzyl ester composition comprising 2,2-dimethyl-4,5-benzospiro[2,4]hepta-4,6-diene-1-carboxylic acid, α-cyano-m-phenoxybenzyl ester and a stabilizer in an amount to effect stabilization of the formula:

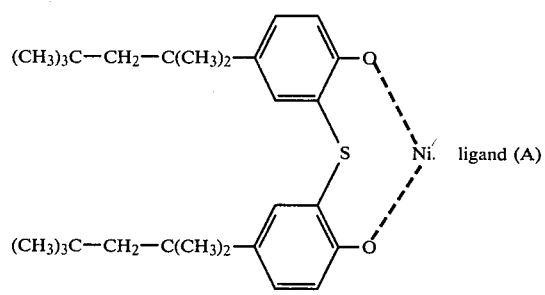

wherein the ligand (A) is an aliphatic primary amine of 4–12 carbon atoms.

5. A composition according to claim 4 wherein the stabilizer is

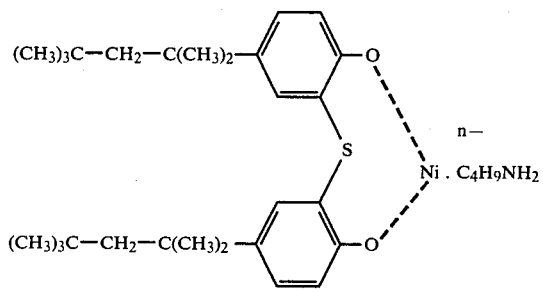

6. A composition according to claim 4 wherein the stabilizer is

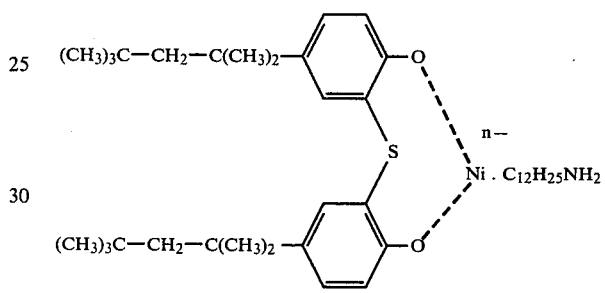

* * * * *